United States Patent
Braendle et al.

(10) Patent No.: US 7,473,897 B2
(45) Date of Patent: Jan. 6, 2009

(54) SYSTEM, METHOD, AND COMPUTER PROGRAM FOR CONDUCTING OPTICAL TRANSMISSION MEASUREMENTS AND EVALUATING DETERMINED MEASURING VARIABLES

(75) Inventors: Hansjoerg Braendle, Niederuzwil (CH); Erich Nadler, Winterthur (CH); Matthias Graeter, Uetikon a.S. (CH); Daniel Bischof, Rüti (CH)

(73) Assignee: Tecan Trading AG, Mannedorf (CH)

( * ) Notice: Subject to any disclaimer, the term of this patent is extended or adjusted under 35 U.S.C. 154(b) by 395 days.

(21) Appl. No.: 10/487,160

(22) PCT Filed: Mar. 12, 2002

(86) PCT No.: PCT/EP02/10232

§ 371 (c)(1),
(2), (4) Date: Jul. 19, 2004

(87) PCT Pub. No.: WO03/023370

PCT Pub. Date: Mar. 20, 2003

(65) Prior Publication Data

US 2004/0260520 A1    Dec. 23, 2004

(30) Foreign Application Priority Data

Sep. 12, 2001    (CH)    ................... 1681/01

(51) Int. Cl.
G01J 5/02    (2006.01)
G01N 21/00    (2006.01)
G01F 23/00    (2006.01)

(52) U.S. Cl. .................. 250/343; 250/357.1; 356/435; 702/55

(58) Field of Classification Search ............ 356/435; 250/357.1, 577, 343; 702/55

(56) References Cited

U.S. PATENT DOCUMENTS 4,119,860 A    10/1978    Gooley
4,260,883 A    4/1981    Onoda et al.

(Continued)

FOREIGN PATENT DOCUMENTS

JP    04-372861 A    12/1992

(Continued)

*Primary Examiner*—David P Porta
*Assistant Examiner*—Carolyn Igyarto
(74) *Attorney, Agent, or Firm*—Notaro & Michlaos P.C.

(57) ABSTRACT

A device for conducting a transmission measurement includes a system for generating a light wave consisting of a first and a second wavelength fraction, in addition to an optical channel guiding the light wave to a sample tube with a sample, wherein the light wave permeates the sample tube with a sample. The device also has a motion unit for producing a relative movement of the light wave along the sample tube. A receiver for receiving and separating the first and second wavelength fragments after the light wave has permeated the sample tube with a sample is also provided. A converter converts the first wavelength fraction into a first digital measuring value describing the degree of transmission in the first wavelength and converts the second wavelength fraction into a second digital measuring value describing the degree of transmission in the second wavelength. Quotients are formed from the first digital measuring values and the second digital measuring values by an evaluation system and the first derivative of the quotients is calculated.

20 Claims, 4 Drawing Sheets

U.S. PATENT DOCUMENTS

| | | | |
|---|---|---|---|
| 4,873,875 A | | 10/1989 | Cork |
| 4,899,053 A | * | 2/1990 | Lai et al. .................... 250/343 |
| 5,124,553 A | * | 6/1992 | Hilliard et al. .............. 250/344 |
| 5,245,292 A | | 9/1993 | Milesky et al. |
| 5,463,228 A | * | 10/1995 | Krause ....................... 250/577 |
| 6,235,534 B1 | | 5/2001 | Jacobs et al. |
| 6,770,883 B2 | * | 8/2004 | Mc Neal et al. .......... 250/341.1 |
| 6,806,947 B1 | * | 10/2004 | Ekdahl et al. ................ 356/39 |
| 2003/0058450 A1 | * | 3/2003 | Mosley et al. .............. 356/436 |

FOREIGN PATENT DOCUMENTS

| | | |
|---|---|---|
| WO | 00/67547 A2 | 11/2000 |

* cited by examiner

SYSTEM, METHOD, AND COMPUTER PROGRAM FOR CONDUCTING OPTICAL TRANSMISSION MEASUREMENTS AND EVALUATING DETERMINED MEASURING VARIABLES

CROSS-REFERENCE TO RELATED APPLICATIONS

This application claims priority on Swiss Patent Application No. CH 1681/01 and International Application PCT/EP02/10232, filed on 12 Sep. 2002, which is incorporated herein by reference.

FIELD AND BACKGROUND OF THE INVENTION

The present invention relates to performing optical transmission measurements and analyzing signals which are provided in this case. In particular, it relates to the automated performance and analysis of transmission measurements on sample tubes.

In laboratories which are concerned with molecular biological/biochemical assays of sera or other human, animal, or plant bodily fluids, secretions, or excrements, for example, the samples to be investigated are often provided in a sample tube. The sample tubes are typically provided with a label which is used for assigning the sample to the individual from whom the sample originates. Typically, these labels also contain a computer-readable barcode or another machine-readable inscription.

Even before the actual—often time-consuming—molecular biological/biochemical assay, the samples are pre-assayed so that poor samples or samples which are not to be processed further are sorted out and/or so that the samples may be sorted in accordance with the further processing. This pre-assay is typically performed on the basis of irradiation of the samples using light and is to be performed rapidly and automatically. For this purpose, care is often taken that at least a narrow strip along the tube in which these samples are located is not covered by a label, so that the samples may be irradiated more easily. However, it often happens that either the labels are selected too large or the tube diameter is selected too small and therefore—because of the overlap of the label on the circumference of the sample tube—the sample is no longer visible from the outside. Most known systems for the pre-assay irradiation of such samples typically fail in the object of performing an automatic pre-assay even on such "hidden samples". Other systems are very expensive and complex.

Swiss priority application no. CH 1681/01, filed Sep. 12, 2001, entitled "Optical device, system, and application", describes a system which allows an automatic pre-assay to be performed on the samples even if the samples are not visible from the outside because of the labels which cover the sample tube completely, for example. For this purpose, a system was developed having two light sources, which emit light of different wavelengths in the near-infrared range. In addition, this system includes an optical device for mixing this light.

The achievement of the object according to the present invention is based on the consideration that, for example, blood serum behaves very similarly to water in regard to the absorption of light in the near-infrared wavelength range. Therefore, the characteristic transmission behavior of water may be exploited for the detection of serum. As a consequence, the following are referred to as serum: hemolytic serum, lipemic (fat-containing) serum, bilirubin serum, lymph, and urine, to give a few common examples.

The transmission curves of all phase-forming components of blood, i.e., serum and blood clots, for example, but also the transmission of all other materials present in the sample tube, such as air, glass, plastic cover, gels, and granulates, were recorded in the wavelength between 950 nm and 1450 nm using irradiation of blood samples with light. In addition, these measurements were repeated, but the samples were covered with barcode strips. Subsequently, two wavelength ranges were determined in the transmission range in which a clear separation between "serum" and "not serum" is possible. These ranges are between 1200 nm and 1400 nm for a first light source and between 1000 nm and 1110 nm for a second light source. Light sources in which the wavelength of the light of the first light source is 1250 nm and/or 1300 nm and the wavelength of the light of the second light source is approximately 1070 nm are especially preferred.

Due to the different transmission values of the samples (caused by the samples themselves) and due to the different combinations of labels on the tubes, a very high amplification range of the measurement signal captured after passing through the sample is necessary. Barcodes printed on the labels, which are also to be illuminated through, make this even more difficult. Illuminating light through the sample at exactly the same location—i.e., a sample illumination which is identical in relation to the spatial distribution and the angular distribution having quasi-localized coherence—using light of different wavelengths is absolutely necessary for this purpose, since the measurement result would be corrupted through spatial deviations.

After the light from two or more light-emitting diodes (LEDs) or laser diodes (LDs) is irradiated through the sample simultaneously and at the same location, the corresponding signals are detected and supplied to an analysis. In this case, a unique parameter is determined after the measurement of the transmission value by producing a quotient of the first light source to the second light source. This parameter may be used for the purpose of making a statement about the presence of serum.

SUMMARY OF THE INVENTION

The sample is to be movable in relation to the measurement arrangement, or the measurement arrangement is to be movable in relation to the sample, in such a way that a sequence of measurements along the (normally stationary) sample tube, and therefore a uniform rasterizing of the sample in fine measurement steps, is made possible. The analysis must support this type of transmission measurement.

The object of the present invention is to suggest a simple, alternative method and a corresponding apparatus which allow an automatic transmission measurement to be performed on samples.

It is a further object of the present invention to provide a control program for controlling the analysis of an optical transmission measurement using a computer or a digital signal processor (DSP) and a corresponding computer program product which may be loaded in an apparatus having a computer or digital signal processor.

These requirements are fulfilled according to the present invention by an apparatus according to independent claim 1.

These requirements are fulfilled according to the present invention by the method according to independent claim 14.

These requirements are fulfilled according to the present invention by the control program according to independent claim 25 and by the computer program product according to independent claim 29.

Measurements/assays may be performed with high reproducibility according to the present invention. The apparatus allows rapid and reliable functioning without manual intervention. The recognition of "serum" and/or "not serum" allows automation/simplification of numerous processes e.g., in the laboratory or clinical fields.

Further advantages of the present invention result from the following description.

BRIEF DESCRIPTION OF THE DRAWINGS

The following schematic figures are to explain preferred embodiments of the apparatus and/or the system according to the present invention, without restricting the scope of the present invention. In this case.

DESCRIPTION OF THE PREFERRED EMBODIMENTS

Figure 1:
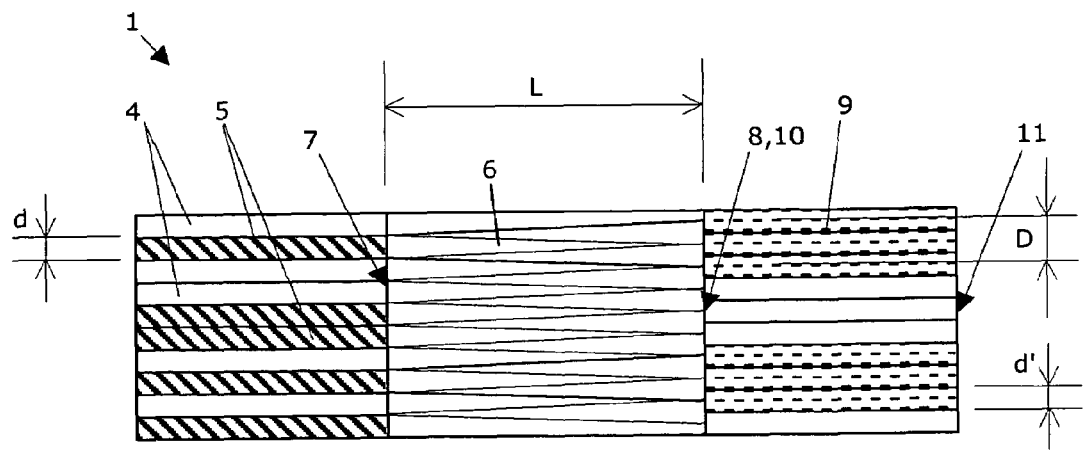
FIG. 1 shows a longitudinal section through a round mixing block.

FIG. 1 shows a longitudinal section through a round mixing block which is suitable for use in a device for performing a transmission measurement according to the present invention. This mixing block is part of an optical device 1 for mixing light of different wavelengths. This device 1 is connectable to at least two light sources 2, 3, the first light source 2 emitting light having a first wavelength and the second light source 3 emitting light having a second and/or further wavelength. The device 1 includes a first light guide fiber bundle 4 for conducting the light of the first wavelength and a second and/or further light guide fiber bundle 5 for conducting the light of the second and/or further wavelength, as well as a mixing block 6. This mixing block 6 has an immission surface 7 and an emission surface 8. The fibers of the light guide fiber bundle 4, 5 have a diameter (d), they are preferably statistically intermingled with one another, and—through the densest possible packing—positioned essentially parallel to one another. For simultaneous feeding of the two or more different wavelengths into the mixing block 6, the light guide fiber bundles 4, 5 are attached to the immission surface 7 of the mixing block 6. The light guide fibers preferably have an essentially perpendicular end surface, which is then attached plane-parallel to the immission surface 7. A screw or plug-in connection is especially preferred, which guarantees a closely fitting seat of the light guide fibers on the immission surface and which also provides a light-tight sheathing of the connection. The mixing block 6 has—for expanding the light beam incident from each light guide fiber of the bundles 4, 5 to a light spot having a diameter (D)—at least an optically active length (L). The mixing block 6 may have any arbitrary shape suitable for relaying the incident light and may therefore be implemented as straight, bent, and/or at least partially curved, having an essentially uniform or changing cross-section, but even as a polygon, for example.

Upon entry into the mixing block 6, the diameter of the light beam essentially corresponds to the diameter d of the light guide fibers. In the light guide rod, each light beam expands so that it—after traversing a specific, optically active mixing block length (L)—generates a light spot having the diameter (D) on the outlet or emission surface.

There are many possibilities for dimensioning the mixing block 6, mixing blocks which do not require any optical lenses or mirrors being preferred. In this way, the production costs may be reduced and, in addition, the risk of lenses and/or mirrors coming out of alignment—because of vibrations in the system, for example—is excluded. In addition, the number of transition surfaces for each light beam is lowered. Furthermore, achievements of the object which exploit the total reflection of the light in the light guides and in the mixing space and/or mixing block are preferred.

If a dense, hexagonal packing and optimum intermingling of the first and second light guide fiber bundles 4, 5 are assumed, each fiber has on average an equal number of identically colored neighbors; in practice, however, even good statistical mixing is sufficient. In the case in which a further fiber bundle is optimally intermingled with the light guide fiber bundles 4, 5, none of the light guide fibers has a neighbor which conducts light having the same wavelength.

Figure 2:
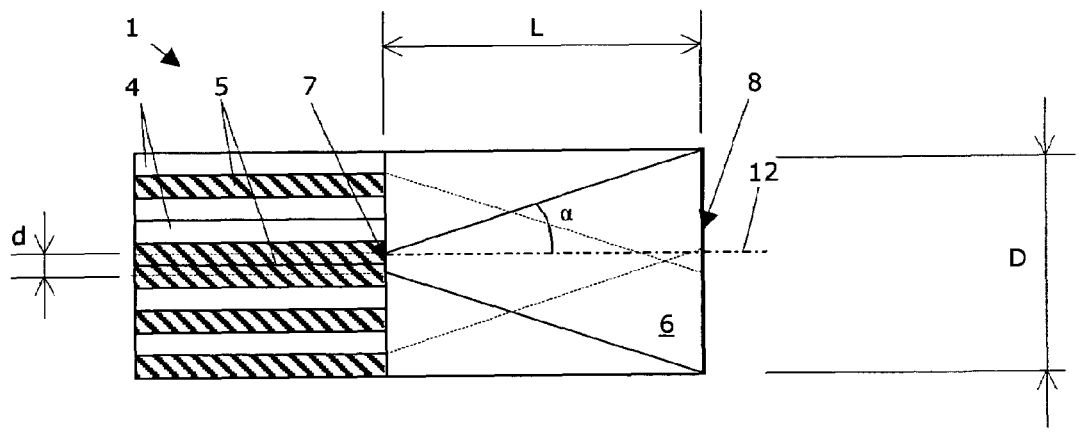
FIG. 2 shows a longitudinal section through a different type of mixing block.

FIG. 2 shows a longitudinal section through a different type of mixing block which is suitable for use in a device for performing a transmission measurement according to the present invention. The intermingling of the light guide fiber bundles 4, 5 and their connection to the mixing block 6 corresponds to the first embodiment in FIG. 1. The embodiment shown in FIG. 2 has the advantage in relation to that in FIG. 1 that even if the light guide fiber bundles 4, 5 are not intermingled optimally, but merely statistically, a sufficient mixed light quality results. Through the total reflection at the side surfaces of the mixing block 6, an expanded light beam originating from a light guide fiber at the edge covers at least half of the emission surface 8 (cf. FIG. 2: light beams, which enter from the fibers at the edge, indicated in the mixing block 6 by points).

FIG. 2 also differs from FIG. 1 in that no light guide fiber bundle is attached to the emission surface 8 of the mixing block. In the first embodiment (FIG. 1), the mixing block 6 is a round light guide rod, in which immission surface 7 and emission surface 8 are equally large and essentially correspond to the rod cross-section. The third light guide fiber bundle 9 has an essentially round starting surface 10 and an end surface 11 which is implemented as essentially rectangular. In the second embodiment, the mixing block 6 is a light guide rod in which immission surface 7 and emission surface 8 are essentially equally large, the immission surface 7 being implemented as essentially round and the emission surface 8 as essentially rectangular. Therefore, the active light cross-section is changed with the aid of the third light guide fiber bundle 9 in the first embodiment, while in the second embodiment, in contrast, it is changed with the aid of the mixing block 6.

Notwithstanding the embodiments shown, the shape of the immission and/or emission surfaces of the mixing block 6 may deviate from a round disk and have, for example, an oval, polygonal, or mixed shape having straight and curved edges. In addition, the immission and emission surfaces may have different areas. Optionally, as shown, a third light guide fiber bundle 9 may be dispensed with.

Figure 3:
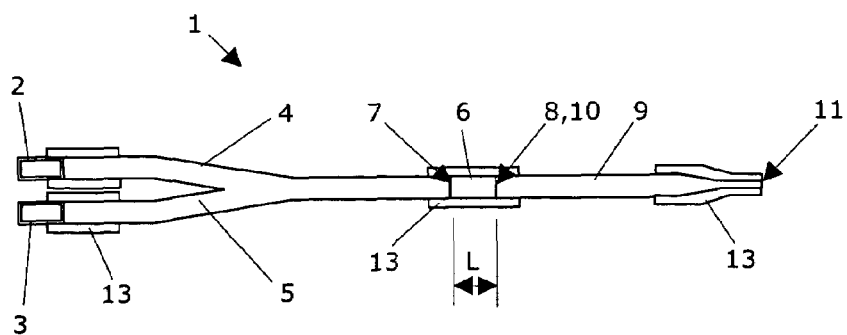
FIG. 3 shows an overview illustration of the light guides from the light sources up to the illumination area, according to the first embodiment of the mixing block.

FIG. 3 shows an overview illustration of the light guides from the light sources up to the illumination surface according to the first embodiment of the mixing block. The optical device 1 for mixing light of different wavelengths is connected to two light sources 2, 3, the first light first 2 emitting light having a first wavelength and the second light source 3 emitting light having a second and/or further wavelength. The device 1 includes a first light guide fiber bundle 4 and a second and/or further light guide fiber bundle 5, as well as a mixing block 6 having an immission surface 7 and emission surface 8. The fibers of the light guide fiber bundles 4, 5 are preferably statistically intermingled with one another, positioned essentially parallel to one another, and—for simultaneous feeding of the different wavelengths—connected to the immission surface 7 of the mixing block 6. The mixing block 6 has—for expanding the light beam incident from each light guide fiber of the bundles 4, 5—at least one optically active length L. Preferably, all connections 13, e.g., to the light sources 2, 3 and the mixing block 6, are implemented so they may be plugged or screwed in and are light-tight.

The properties of the material—e.g., quartz glass, plastic, or other materials typical for the conduction of light having a wavelength from 200 nm to 1400 nm—which is selected for the mixing block determines—together with the wavelengths selected for the first, second, and further light sources—the expansion of the light beam in the mixing block and therefore the dimension for the optically active length L of the mixing block 6 between its immission surface 7 and the emission surface 8.

Figure 4:
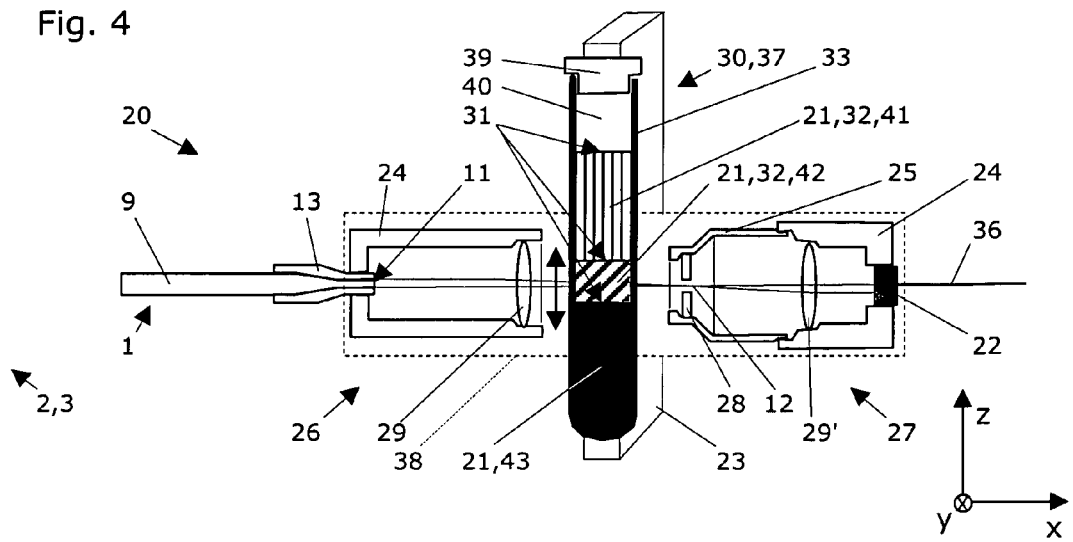
FIG. 4 shows a vertical section through the sample holder and optic of a first system for performing transmission measurements on sample tubes.

FIG. 4 shows a detail from a first device 20 for performing transmission measurements through strongly varying samples 21. A vertical section through the sample holder and optic of a device for performing transmission measurements on sample tubes 30 is shown. The two light sources 2, 3, which emit light having different wavelength components in the near-infrared range (NIR), are not shown. Only the third light guide fiber bundle 9 of an optical device 1 for mixing light of different wavelengths is shown. The device 20 also includes a detector 22 and a sample holder 23. To irradiate mixed light of two wavelengths into a sample 21 with quasi-localized coherence, the device 20 includes an illumination optic 26, which is implemented to receive the emission surface 8 of the mixing block 6 or (as shown) to receive the end surface 11 of the third light guide fiber bundle 9 of the device 1.

In addition, the device 20 includes a receiving optic 27 having an aperture 28—for relaying the light, which penetrates the sample 21 essentially horizontally here, to the detector 22. The two optics 26, 27 each have one or more lenses 29, 29', as required, which are positioned fixed or movably along the optical axis 12. The aperture 28 is used for filtering out scattered light. Preferably, the lenses 29, 29' and the detector 22 are each positioned in a light-tight housing 24. The third light guide fiber 9 discharges in this case into the housing 24 and is preferably screwed thereon and/or plugged into a corresponding seat (not shown) therein. The aperture 28 is also located in a light-tight housing 25, which is preferably movable and/or rotatable in relation to the housing 24 for the lenses 29' and the detector 22, so that the aperture 28 may be adjusted and set for specific operating conditions. A line 36 or a bus conducts the signals generated by the detector to a computer (not shown in FIG. 4), which is described later, where the signals are converted and the corresponding data is stored, processed, and analyzed.

The two optics 26, 27 are connected to one another via a connection element 38, so that they may be shifted jointly in relation to the samples 21 and/or in relation to a sample tube 30 (cf. double arrow). For scanning sample tube 30, the optics 26, 27 are preferably moved in the Z direction, the optics 26, 27 and/or the sample holder 23 (in FIG. 5) preferably also being movable in the X and/or Y directions of a spatial coordinate system.

The wavelength components of the light of the first light source 2 are preferably between 1200 nm and 1400 nm and those of the second light source 3 are preferably between 1000 nm and 1110 nm. Especially preferably, the wavelength of the light of the first wavelength is 1250 nm and/or 1300 nm and the wavelength of the light of the second light source is 1070 nm.

In this case, the sample tube 30 contains solid sample parts, such as blood clots 43, liquid sample parts 32, such as lipemic serum 42 and serum 41, as well as granulates or separating gel and gases, such as air 40. The sample tube 30 has a wall 33 (made of quartz glass, for example) and a stopper 39 (made of plastic or rubber, for example). All of these materials and also their phase boundaries 31 are recognized as "serum" or "not serum" and identified by the detection in the device 20.

The label having the barcode is not shown. However, it is generally typical for the individual barcode strips to run approximately in the horizontal direction for a sample tube 30 held essentially vertically in the sample holder 23 of the device 20 and for the barcode therefore able to be read essentially in the vertical direction. The irradiation of light with quasi-localized coherence prevents the barcode strips on the label and/or the phase boundaries inside the sample from being able to impair the measurement results of one of the selected wavelengths.

It is known that the concentration of a substance which absorbs light and the optical absorption of a liquid containing this substance are linked via the Lambert-Beer law. This Lambert-Beer law is as follows:

$$A = c * \epsilon * l = \log I_0 / I \qquad (4),$$

in which:
A=measured optical absorption
c=concentration of the dissolved material [M=mol/l]
$\epsilon$=molar extinction coefficient of the dissolved material [1/(M*cm)]
l=layer thickness of the liquid which the light must pass through (path length [cm])
$I_0$=intensity of the sample illumination
I=intensity of the light coming out of the sample For a direct calculation of the concentration of a substance—particularly for the vertical transmission through microplates (in FIG. 5), in whose wells the samples are located—the determination of the path length is unavoidable. Because the solvent is water in most biological applications and water has an absorption maximum at 977 nm, the absorption of water may be exploited by using illumination in the near-infrared range (NIR: 750-2500 nm). However, the absorption of water at 977 nm is a function of the sample temperature, so that because of this one often deviates to the isosbestic point of the water and measures the absorption at approximately 998 nm and therefore independently of the sample temperature. Taking the base absorption of water at 900 nm into consideration, and starting from this Lambert-Beer law, the path length and the concentration of the substance in the sample may be calculated backward by irradiating light of the corresponding wavelengths through the sample and measuring the absorption.

Light having 998 nm wavelength (specific absorption of water), light having 900 nm wavelength (base absorption of water), and light having, for example, 280 nm (specific absorption of proteins) and/or 260 nm (specific absorption of nucleic acids) is preferred.

Figure 5:
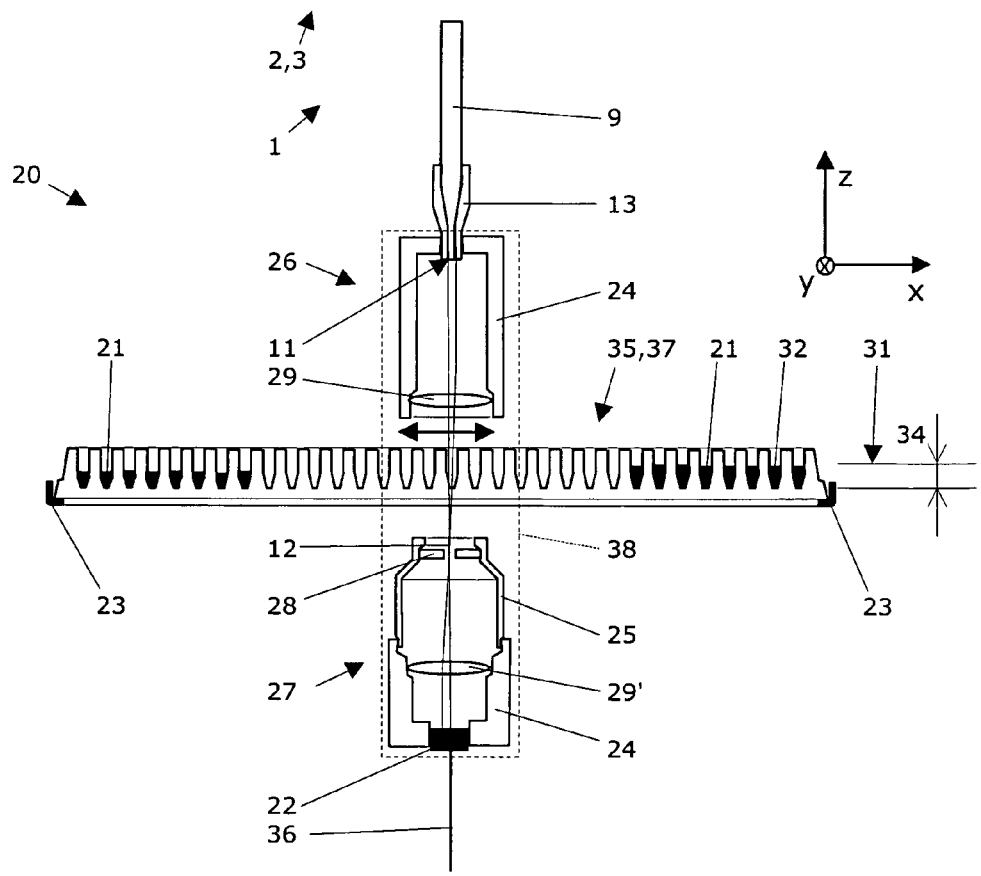
FIG. 5 shows a vertical section through the sample holder and optic of a second system for performing transmission measurements on microplates.

FIG. 5 shows a vertical section through the sample holder and object of a second device for performing transmission measurements on microplates. A microplate 35 is laid in and/or on a specimen stage or sample holder 23, preferably implemented as a frame. The wells of the microplate, which has 96 wells here, for example, are at least partially filled with samples 21. The filling levels 34 may have large differences in this case, as shown; slight differences in the filling levels may also arise for greatly varying reasons. The two light sources 2, 3, which emit light having different wavelength components in the near-infrared range (NIR), and a third light source, which preferably emits light in a range from 200 to 400 nm, as well as any necessary monochromators and/or wavelength filters, are not shown here. Only the third light guide fiber bundle 9 of an optical device 1 for mixing light of different wavelengths is shown. The system 20 also includes a detector 22. For irradiating mixed light of two wavelengths into a sample 21 with quasi-localized coherence, the system 20 includes an illumination optic 26, which is implemented to receive the emission surface 8 of the mixing block 6 or (as shown) to receive the end surface 11 of the third light guide fiber bundle 9 of the device 1.

In addition, the system 20 includes a receiving optic 27 having an aperture 28—for relaying the light, which penetrates the sample 21 essentially vertically here, to the detector 22. The two optics 26, 27 each have one or more lenses 29, 29', as required, which are positioned fixed or movable along the optical axis 12. The aperture 28 is used for filtering out scattered light. Preferably, the lenses 29, 29' and the detector 22 are each positioned in a light-tight housing 24. The third light guide fiber 9 discharges in this case into the housing 24 and is preferably screwed thereon and/or plugged into a corresponding seat (not shown) therein. The aperture 28 is also located in a light-tight housing 25, which is preferably movable and/or rotatable in relation to the housing 24 for the lenses 29' and the detector 22, so that the aperture 28 may be adjusted and set for specific operating conditions. A line 36 or a bus conducts the signals generated by the detector to a computer (not shown here), where these signals are converted and the corresponding data is stored, processed, and analyzed. The analysis of the measured data is performed according to the Lambert-Beer law. The irradiation of light having quasi-localized coherence allows the transmission of light through the samples at exactly the same location, so that the light of each wavelength must cover precisely equal path lengths l through the samples.

The two optics 26, 27 are connected to one another via a connection element 38, so that they may be shifted jointly in relation to the samples 21 and/or in relation to a microplate 35 (cf. double arrow). For scanning microplate 35, which is at least partially filled with liquid 32, the optics 26, 27 may be moved in the X and/or Y directions, the optics 26, 27 and/or specimen stage or sample holder 23 preferably also being movable in the Z direction of a spatial coordinate system. However, the microplate 35 is preferably moved in relation to the two optics 26, 27, which are kept stationary; in this case, a connection element 38 may be dispensed with. The sample holder 23 and optics 26, 27 are especially preferably each implemented as movable and/or adjustable in the X, Y, and Z directions.

In this case, the wavelength components of the light of the first light source 2 are preferably between 900 nm and 1100 nm and those of the second light source 3 are preferably between 800 nm and 1000 nm. Especially preferably, the wavelength of the light of the first light source is 998 nm and the wavelength of the light of the second light source is 900 nm. The wavelength of the light of the third light source is preferably in a range between 200 nm and 1000 nm, wavelengths of 260 nm and/or 280 nm being especially preferred.

The overall analysis or a part of the analysis of the signals, which are provided via the line 36 or via a bus, for example, may be performed by a microprocessor, preferably by a digital signal processor (DSP), which executes a control program. However, the analysis may also be performed using a conventional computer which has been subjected to certain adaptations. The computer must be equipped in such a way that it is capable of digitizing analog signals. Only then are the analysis steps performed, in which the quotients are produced and the first and second derivatives are determined, depending on the application. For this purpose, the computer must have access to a special control program which specifies the execution of the analysis.

Control program is a term which is used in the present context as a synonym for a computer program, in any programming or machine language, or a command set, which is capable of controlling a computer or a DSP in such a way that it executes the desired analysis steps, according to a predetermined flowchart, for example.

The execution of the analysis step may either be performed directly, or the control program may be converted previously or during the analysis into a notation which may be processed by the computer or DSP.

Figure 6:
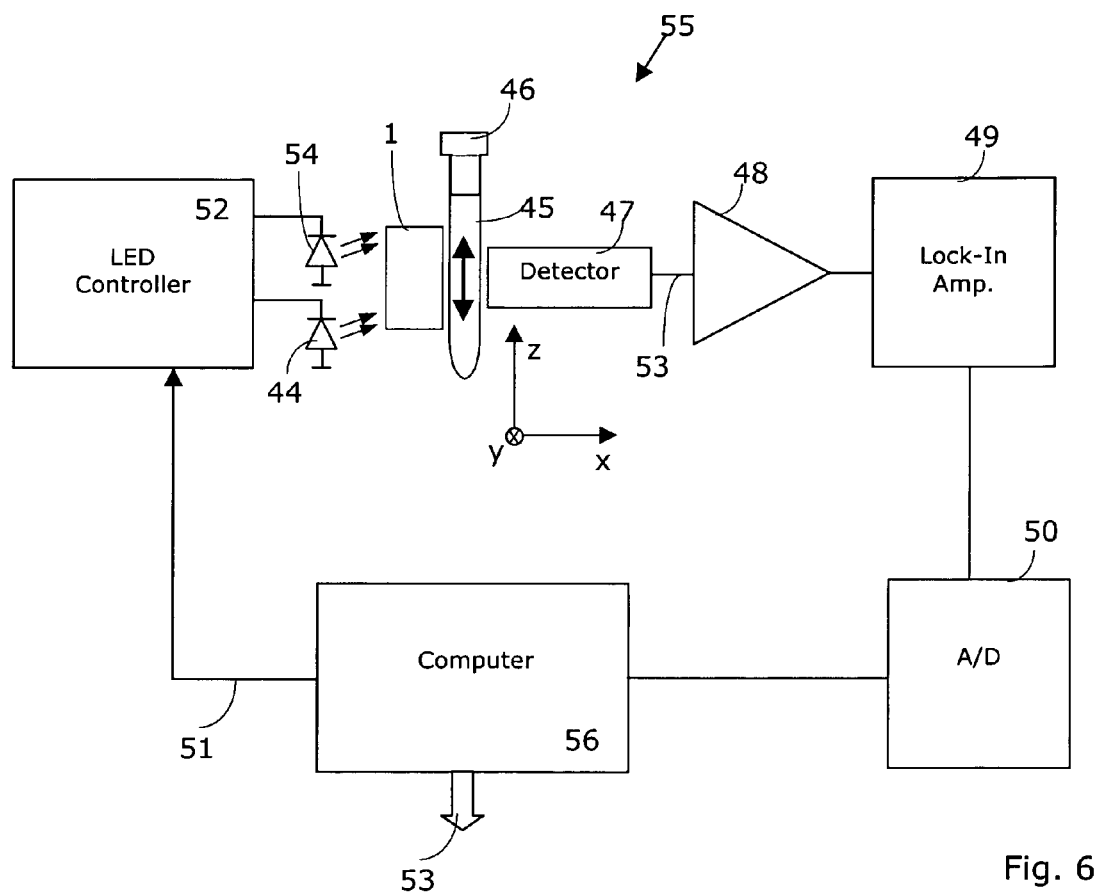
FIG. 6 shows a block diagram of a device for performing a transmission measurement according to the present invention.
Figure 7:
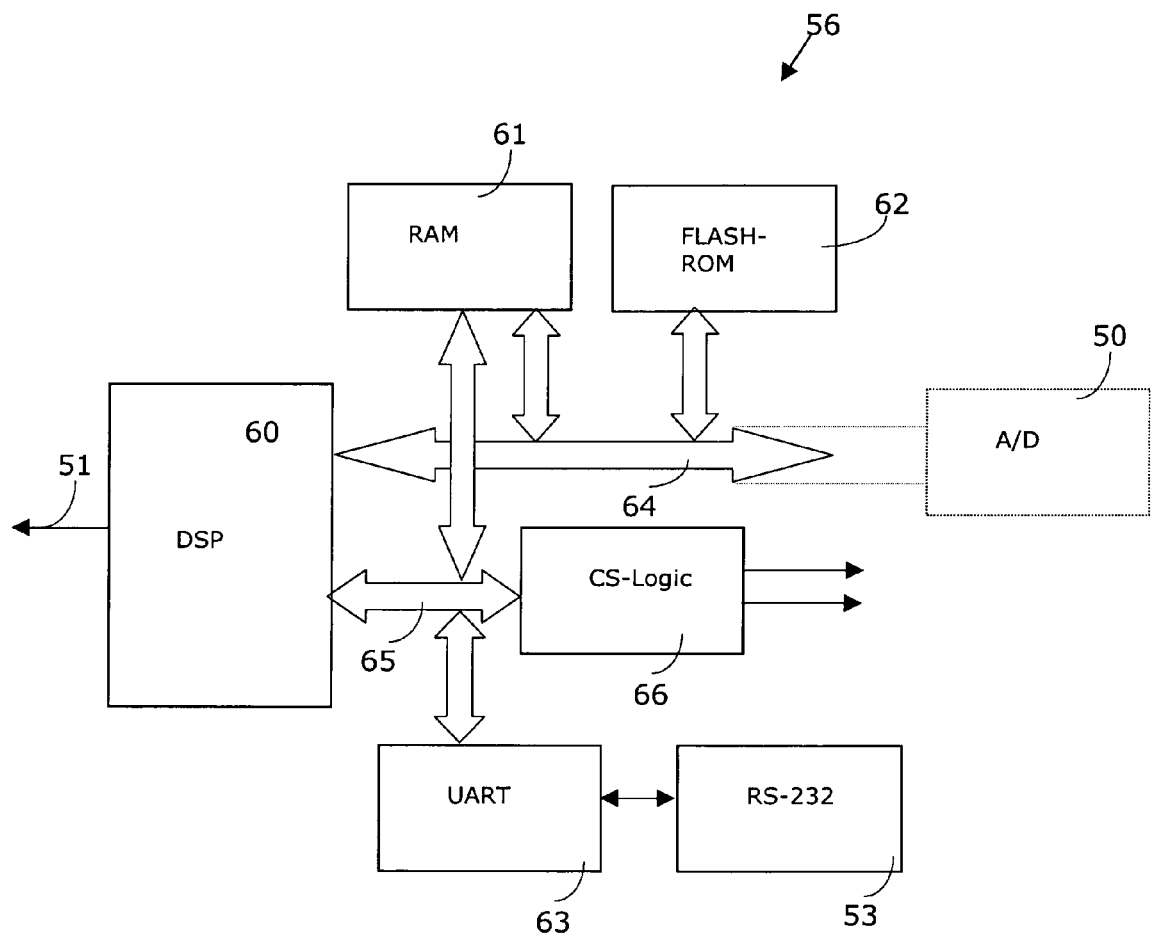
FIG. 7 shows a block diagram of a computer having DSP, according to the present invention.

A first device 55 for performing a transmission measurement is shown in FIG. 6. The device 55 is shown in the form of a schematic block diagram, only the most essential components and connections being shown. It is to be noted that a part of the connection may be bidirectional. Other connections may have multiple lines or channels. The device 55 includes a system 52, 54, 44 for generating a light wave which includes a first and a second wavelength component. In the embodiment shown, the system for generating a light wave includes an LED controller 52, which is controlled by a computer 56 via a multichannel connection 51.

The LED activator may, for example, include a digital/analog converter for converting digital signals into analog signals and a driver stage (e.g., FET output stages) for providing two currents which are supplied to the light-emitting diodes (LEDs) 54 and 44. If the LEDs 54, 44 are activated via the currents, they emit a light wave which has a first and a second wavelength component. For example, it is conceivable that the computer may turn the two LEDs 54, 44 on and off in a targeted way. The light wave is guided via an optical device 1 for mixing light of different wavelengths in the direction of a sample tube 45 having a cover or stopper 46. Optical devices as shown in FIGS. 1-5 are especially suitable. In FIG. 6, the optical device 1 is schematically shown as a single block. The optical device 1 provides an optical channel which guides the light wave to the sample tube 45 having the sample in such a way that the light wave penetrates the sample tube 45 having the sample.

A movement unit is provided (not shown in FIG. 6), which generates a relative movement parallel to the Z axis between the light waves along the sample tube 45. The movement unit may, for example, also generate a rotational movement of the sample tube 45 around the longitudinal axis of the sample tube 45 (parallel to the Z axis), so that the tube 45 may be assayed from different sides. The movement unit may be controlled by the computer 56.

A detector 47 (receiver) for receiving the first and the second wavelength components is positioned on the diametrically opposite side of the sample tube 45. The detector 47 may be equipped with an optic as shown in one of FIGS. 4 or 5, for example. The detector may, for example, have one or more photodiodes. These photodiodes may, for example, be switched over by the computer 56, so that either a first and/or a second photodiode is used. InGaAs photodiodes are well suitable.

In the embodiment shown, the output signals of the detector 47 are transmitted to a pre-amplifier 48, which is in turn connected to a lock-in amplifier 49. Such a pre-amplifier is preferably used when the light signals have been strongly attenuated after penetrating the sample tube. The pre-amplifier may be a commutating pre-amplifier, whose amplification factor is adjustable between $10^3$ and $10^8$ via the computer 56, for example. Through the commutation of the amplification factor, intensity variations of the light source at the input of the detector 47 may be compensated for, for example. It is an object of the pre-amplifier 48 to convert the photodiode currents of the detector 47 (modulated summation signal of the LEDs 54 and 44) into an input voltage usable by the lock-in amplifier 49 and to amplify it. The lock-in amplifier 49 allows separation of the first and second wavelength components using demodulation and/or filtering. In addition, the lock-in amplifier 49 may perform a signal amplification. An amplification factor between 100 and 500 is suitable for this purpose. It is preferably a dual phase lock-in amplifier.

An analog/digital converter 50 is connected downstream from the lock-in amplifier 49. The analog/digital converter 50 may, for example, have a resolution of 12 bits. This converter 50 converts the first wavelength component into first digital measurement values (X), which describe the degree of transmission at the first wavelength, and the second wavelength component into second digital measurement values (Y), which describe the degree of transmission at the second wavelength. The first and second digital measurement values (X, Y) are transmitted to an analysis system, which is implemented in the form of a computer 56 in the example shown. The analysis system produces a quotient from the first digital measurement values (X) and the second digital measurement values (Y), and determines the first derivative of the quotient. The derivative is preferably produced according to the location.

The lock-in amplifier 49 is preferably connected via an X-channel and a Y-channel to the analog/digital converter 50. The device 55 is preferably designed in such a way that the analysis system (computer 56) may determine the position of a boundary surface inside the sample in the sample tube 45 on the basis of the first derivative. In addition, the boundary surface may be determined by analyzing a first and a second zero crossing of the first derivative and the zero crossing of the second derivative, which lies between the zero crossings of the first derivative. It is to be noted here that in principle the boundary surface may be determined solely with the aid of the first derivative. However, the achievement of the object described, in which the second derivative is also used, is more precise.

The device 55 is preferably designed in such a way that the analysis system (computer 56) may determine the second derivative of the quotient.

According to a further embodiment of the device 55, the filling level may be determined by analyzing the second derivative in order to determine the point of the first derivative at which the first derivative assumes an absolute minimum.

The LED controller 52 preferably includes a modulator which modulates the first wavelength component and the second wavelength component in order to generate a light wave, which is then supplied to the sample tube via an optical device 1.

The LEDs 54 and 44 are preferably LEDs which emit light having near-infrared wavelengths. The wavelength components of the light of the first light source 54 are preferably between 1200 nm and 1400 nm and those of the second light source 44 are preferably between 1000 nm and 1110 nm.

The LEDs 54, 44 may either be operated at the same frequency (e.g., at 3 kHz) with 90° phase shift (mode 1) or at different frequencies (e.g., 3 kHz and 1.5 kHz) without phase shift (mode 2). The LEDs 54, 44 are operated for example using square-wave signals.

In mode 1, the lock-in amplifier is operated as a real dual channel lock-in amplifier using the two frequencies (e.g., 3 kHz and 1.5 kHz). In mode 2, in contrast, the lock-in amplifier is operated as a dual channel lock-in amplifier using one frequency, which is phase shifted by 90°, however.

The analysis system preferably includes a digital signal processor (DSP). This DSP may, for example, be integrated in the computer or plugged therein using a plug-in card.

Details of a computer 41 having DSP 60 are shown in FIG. 8. This is an exemplary, schematic illustration. The DSP 60 is connected via an address bus 65 and a data bus 64 to the various elements of the computer 41. There is a flash-ROM 62, in which the control program and possibly other preset data and/or parameters are stored. In addition, there is a conventional RAM 61. A chip select (CS) logic 66 is used in order to activate external components of the device 40. RC elements (not shown in FIG. 8) may be provided between the DSP and the connection 51 to the LED controller 42, in order to be able to eliminate interfering spikes. There is a universal asynchronous receiver/transmitter (UART) component 63 to administrate the serial RS-232 interface 54. The A/D converter 50 of the device 40 is connected from the outside to the data bus 64, as is indicated by the dashed lines.

The analysis system may be designed in such a way that the first digital measurement values (X) and the second digital measurement values (Y) may be input, stored, and analyzed. The analysis system may additionally include a memory for storing the control codes which are used to control the digital signal processor (DSP). The computer 56 is preferably designed having a bus interface (e.g., in the form of an RS-232 interface).

In a special embodiment, the DSP assumes the following functions and control tasks, for example:
  modulation of the LEDs 54, 44;
  input of the digital measurement signals (X, Y);
  commutation of the amplification factor of the pre-amplifier 48;
  possible input of an overload bit (in case of an overload, this may be displayed in order to then reduce the amplification factor) from the pre-amplifier 48;
  calculation of the separation level and/or the filling level;
  determination of the cap type 46;
  activation of the motors for movement parallel to the Z-axis during a measurement cycle;
  communication with another system, e.g., a master system;
  switching between different photodiodes of the detector 47.

The method according to the present invention includes at least the following steps:
  generating a light wave which includes a first and a second wavelength component,
  illuminating a sample tube filled with the sample using the light wave while a relative movement of the light wave along the sample tube is performed;
  receiving the first and second wavelength components (as a summation signal) after the light wave has penetrated through the sample tube having the sample, separating the first and second wavelength components, converting the first wavelength component into first digital measurement values (X), which describe the degree of transmission at the first wavelength, converting the second wavelength component into second digital measurement values (Y), which describe the degree of transmission at the second wavelength, producing the quotients of the first digital measurement values (X) and the second digital measurement values (Y), and determining the first derivative of the quotients.

According to the present invention, the position of a boundary surface inside the sample in the sample tube may be determined by producing and analyzing the first derivative of the quotients. Furthermore, according to the present invention, the boundary surface may be determined by analyzing a first and a second zero crossing of the first derivative. In one embodiment of the present invention, the position of the boundary surface may be output, this preferably being performed on a display screen or a printer.

The filling level of the sample in the sample tube may be determined according to the present invention by producing and analyzing the second derivative. In one embodiment of the present invention, the filling level may be output, this preferably being performed on a display screen or a printer.

During the determination of the first derivative, a search window is preferably defined in order to exclude a part of the quotients from the determination of the first derivative and therefore make the process more rapid and/or less computer-intensive.

The application of the present invention is not restricted to sample tubes. It may also be used in connection with other sample containers.

Any arbitrary combinations of the embodiments shown and/or described are included in the scope of the present invention, even if these combinations are not explicitly shown. The reference numbers in all figures identify the same elements in each case, even if these elements are not always explained individually.

What is claimed is:

1. An apparatus for performing transmission measurements on sample tubes, the apparatus comprising:

a first light source that generates light with a first near-infrared range wavelength as a first wavelength component;

a second light source that generates light with a different and second near-infrared range wavelength as a second wavelength component;

an optical device for mixing the first and second wavelength components of the two light sources and for guiding these wave-length components into an optical channel;

the optical channel guides the mixed first and second wavelength components to a sample tube having a sample in such a way that the different wavelength components penetrate the sample tube with the sample at exactly the same location;

a movement unit for generating a relative movement between the optical channel and the sample tube with the sample, a receiver for detecting the intensity of the first and second wavelength components after penetration of the sample tube with the sample and for generating detection signals for the first and second wavelength components;

converters for converting the detection signals for the first wavelength component into first digital measurement values (X) that describe the degree of transmission at the first wavelength, and for converting the detection signals for the second wavelength component into second digital measurement values (Y) that describe the degree of transmission at the second wavelength; and an analysis system for analyzing the measurement values by producing a quotient from the first digital measurement values (X) and the second digital measurement values (Y); and for determining a first derivative of the quotient;

wherein the corresponding measurement values (X) and (Y) are obtained with respect to position during relative movement between the sample tube with the sample and the optical channel, so that the derivative of the quotient is obtained from corresponding spatial coordinates, which enables the apparatus, following the processing and analysis of the measurement values (X) and (Y), to determine the position of at least one boundary surface between two phases or density zones of the sample or the filling level in the sample tube.

2. The apparatus according to claim 1, wherein the first light source and the second light source include light-emitting diodes that emit the first wavelength component or the second wavelength component, respectively.

3. The apparatus according to claim 2, including a modulator that modulates the first wavelength component and the second wavelength component.

4. The apparatus according to claim 1, wherein the first light source emits light with a wavelength between 1200 nm and 1400 nm and the second light source emits light with a wavelength between 1000 nm and 1110 nm.

5. The apparatus according to claim 4, wherein the wavelength of the first light source is 1250 nm or 1300 nm and the wavelength of the second light source is 1070 nm.

6. The apparatus according to claim 1, wherein the receiver includes a pre-amplifier, the pre-amplifier having an adjustable amplification factor and a connection to a digital signal processor, for compensating for intensity variations of the light wave at the input of the receiver.

7. The apparatus according to claim 1, wherein the receiver has a lock-in amplifier for separating the first and second wavelength components using one of demodulation and filtering.

8. The apparatus according to claim 1, including a digital signal processor, which inputs, stores, and analyzes the first digital measurement values (X) and the second digital measurement values (Y).

9. The apparatus according to claim 8, wherein the analysis system includes a memory for storing a control code that is used to control the digital signal processor.

10. A method for performing a transmission measurement on sample tubes, comprising the steps of:

generating light with a first near-infrared range wavelength as a first wavelength component using a first light source;

generating light with a different and second near-infrared range wavelength as a second wavelength component using a second light source;

mixing the first and second wavelength components of the two light sources with an optical mixing device and feeding the mixed first and second wavelength components into an optical channel by the optical mixing device;

guiding the mixed wavelength components to a sample tube using the optical channel in such a way that the different wavelength components of the light wave penetrate the sample tube with a sample at exactly the same location;

illuminating a sample tube with the sample using the different wavelength components at exactly the same location while a relative movement of the optical channel and the sample tube with the sample is performed;

receiving and detecting the first and second wavelength components after penetration through the sample tube with the sample;

generating detection signals for the first and second wavelength components;

converting the detection signals for the first wavelength component into first digital measurement values (X) that describe the degree of transmission at the first wavelength;

converting the detection signals for the second wavelength component into second digital measurement values (Y) that describe the degree of transmission at the second wavelength;

producing quotients of the first digital measurement values (X) and the second digital measurement values (Y); and determining a first derivative of the quotients;

wherein the corresponding measurement values (X) and (Y) are obtained with respect to position during relative movement between the sample tubes and the optical channel, so that the derivative of the quotient is obtained from corresponding spatial coordinates, in such a way that this apparatus determines the position of at least one boundary surface between two phases or density zones of the sample or the filling level in the sample tube.

11. The method according to claim 10, wherein determining the boundary surfaces is executed by analyzing a first and a second zero crossing of the first derivative of the quotients of the first digital measurement values (X) and the second digital measurement values (Y), according to the corresponding spatial coordinates.

12. The method according to claim 10, wherein determining the filling level of the sample in the sample tube is executed by analyzing the second derivative of the quotients of the first digital measurement values (X) and the second digital measurement values (Y), according to the corresponding spatial coordinates.

13. The method according to claim 10, wherein a demodulation is performed to separate the first and second wavelength components.

14. The method according to claim 10, wherein a search window is defined before the step to determine the first derivative of the quotients of the first digital measurement values (X) and the second digital measurement values (Y), according to the corresponding spatial coordinates, in order to exclude a part of the quotients from the determination of the first derivative.

15. A method for automatically determining a boundary surface inside a sample which is located in a sample tube, wherein the method is performed according to claim 11 and the position of the boundary surface is output on a display screen or a printer.

16. A method for automatically determining the filling level of a sample which is located in a sample tube, wherein the method is performed according to claim 12 and the position of the filling level is output on a display screen or a printer.

17. A computer readable medium comprising a control program for controlling an apparatus for performing an optical transmission measurement on sample tubes and for the analysis of the optical transmission measurement using a computer or a digital signal processor (DSP), into which the control program is loaded, wherein the computer or the digital signal processor, in which the control program is activated, controls the apparatus to execute the following steps:

generating light with a first near-infrared range wavelength as a first wavelength component using a first light source;

generating light with a different and second near-infrared range wavelength as a second wavelength component using a second light source;

mixing the first and second wavelength components of the two light sources with an optical mixing device and feeding the mixed first and second wavelength components into an optical channel by the optical mixing device;

guiding the mixed wavelength components to a sample tube using the optical channel in such a way that the different wavelength components of the light wave penetrate the sample tube with a sample at exactly the same location;

illuminating a sample tube with the sample using the different wavelength components at exactly the same location while a relative movement of the optical channel and the sample tube with the sample is performed;

receiving and detecting the first and second wavelength components after penetration through the sample tube with the sample;

generating detection signals for the first and second wavelength components;

converting the detection signals for the first wavelength component into first digital measurement values (X) that describe the degree of transmission at the first wavelength;

converting the detection signals for the second wavelength component into second digital measurement values (Y) that describe the degree of transmission at the second wavelength;

producing quotients of the first digital measurement values (X) and the second digital measurement values (Y); and determining a first derivative of the quotients;

wherein the corresponding measurement values (X) and (Y) are obtained with respect to position during relative movement between the sample tubes and the optical channel, so that the derivative of the quotient is obtained from corresponding spatial coordinates, in such a way that this apparatus determines the position of at least one boundary surface between two phases or density zones of the sample or the filling level in the sample tube.

18. The computer readable medium according to claim 17, wherein the computer or the digital signal processor, in which the control program is activated, controls the apparatus to execute the following step:

determining the filling level of the sample in the sample tube by producing the second derivative of the quotients of the first digital measurement values (X) and the second digital measurement values (Y), according to the corresponding spatial coordinates.

19. The computer readable medium according to claim 17, wherein the computer or the digital signal processor executes the following step:

controlling the sequence of the transmission measurement.

20. The computer readable medium according to claim 17, wherein the control program is loadable in an apparatus having a computer or digital signal processor, and wherein the control program comprises the following modules:

a module for registering the first digital measurement values (X), which describe the degree of transmission of a sample in the sample tube at a first wavelength, and for registering the second digital measurement values (Y), which describe the degree of transmission of the sample of the sample tube at a second wavelength;

a module for producing the quotients of the first digital measurement values (X) and the second digital measurement values (Y); and a module for determining the first derivative of the quotients.

* * * * *